US006998261B2

(12) United States Patent
Dawson et al.

(10) Patent No.: US 6,998,261 B2
(45) Date of Patent: *Feb. 14, 2006

(54) FUNCTIONAL GENE ARRAY IN YEAST

(75) Inventors: Dean Dawson, Jamaica Plaine, MA (US); John Swindle, Seattle, WA (US)

(73) Assignee: CompleGen, Inc., Seattle, WA (US)

( * ) Notice: Subject to any disclaimer, the term of this patent is extended or adjusted under 35 U.S.C. 154(b) by 403 days.

This patent is subject to a terminal disclaimer.

(21) Appl. No.: 10/149,562

(22) PCT Filed: Dec. 8, 2000

(86) PCT No.: PCT/US00/33329

§ 371 (c)(1),
(2), (4) Date: Jun. 9, 2002

(87) PCT Pub. No.: WO01/42446

PCT Pub. Date: Jun. 14, 2001

(65) Prior Publication Data

US 2002/0182709 A1 Dec. 5, 2002

Related U.S. Application Data

(63) Continuation of application No. 09/459,752, filed on Dec. 10, 1999, now Pat. No. 6,232,074.

(51) Int. Cl.
*C12N 1/19* (2006.01)

(52) U.S. Cl. .............................. 435/254.2; 435/254.21; 435/6; 435/483

(58) Field of Classification Search .............. 435/254.2, 435/254.21, 6, 483
See application file for complete search history.

(56) References Cited

U.S. PATENT DOCUMENTS

| | | | |
|---|---|---|---|
| 5,854,018 A | 12/1998 | Hitzeman et al. | |
| 5,879,926 A | 3/1999 | Lemoine et al. | |
| 5,919,651 A | 7/1999 | Hitzeman et al. | |
| 5,977,305 A | 11/1999 | Wigler et al. | |
| 6,232,074 B1 * | 5/2001 | Dawson et al. ................ | 435/6 |

FOREIGN PATENT DOCUMENTS

WO      WO 99 24603 A      5/1999

OTHER PUBLICATIONS

Alani, Eric et al., "A Method for Gene Disruption that Allows Repeated Use of *URA*3 Selection in the Construction of Multiply Disrupted Yeast Strains", Genetics (Aug. 1987) 116:541–545.
Broach, James R. et al., "Transformation in Yeast: Development of a Hybrid Cloning Vector and Isolation of the *Can*1 Gene", Gene,(1979) 8: 121–133.
Flatters, Michele et al., "*SID1–1*: A Mutation Affecting Meiotic Sister–Chromatid Associate in Yeast", Genetics (1993) 134:423–433.
Giaver, Guri et al., "Genomic profiling of drug sensitivities via induced haploininsufficiency", nature genetics, (1999)21:278–283.
Henikoff, Steven et al., "Isolation of a gene from *Drosophila* by complementation in yeast", Nature (1981) 289, 1/8, 33–37.
Hinnen, Albert et al., "Transformation of yeast", Proc. Natl. Acad. Sci USA, (1978) 75(4):1929–1933.
Kassir, Yona et al., "Monitoring Meiosis and Sporulation in *Saccharomyces cerevisiae*", Methods in Enzymology, vol. 194:94–110.
Kranz, Janice E. et al., "Cloning by function: An alternative approach for identifying yeast homologs of genes from other organisms", Proc. Natl. Acad. Sci USA (1990) 87:6629–6633.
Rose, Mark D., "Isolation of Genes by Complementation in Yeast", Methods in Enzymology, vol. 152:481–504.
Greene Al, Snipe Jr, Gordenin DA, Resnick MA: "Functional analysis of human FEN1 in *Saccharomyces cerevisiae* and its role in genome stability" Human Molecular Genetics, vol. 8, No. 12, Nov. 1999, pp. 2263–2273, XP002189015, "Media and strains," p 2270.
Hartwell LH, Szankasi P, Roberts CJ, Murray AX, Friend SH: "Integrating genetic approaches into the discovery of anticancer drugs" SCIENCE, vol. 278, Nov. 7, 1997, pp 1064–1068, XP002916842).
McNabb D.S., Pak S.M., Guarente L.: "Cassette for the generation of sequential gene disruptions in yeast *Schizosaccharomyces pombe*," BIOTECHNIQUES, vol. 22, No. 6, Jun. 1997, pp 1134–1139, XP000999190 "Abstract" the whole document.
Oliver S.G., Winson M.K., Kell D.B., Baganz F.:"Systematic functional analysis of the yeast genome": Trends in Biotechnology, vol. 16, No. 9, Sep. 1998, pp 373–378, XP004173182, "Generation of specific deletion mutants," p 374.
Paluh JL, Clayton DA: "Mutational analysis of the gene for *Schizosaccharomyces pombe* RNase MRP RNA, mrp1, using plasmid shuffle by counterselection on Canavanine," YEAST, vol. 12, No. 14, Nov. 1996, pp 1393–1405, XP001000809, p 1400; table 3, p 1397, col. 2, line 18–line 27; table 3, p 1394, line 4–line 8 "ABSTRACT".

* cited by examiner

*Primary Examiner*—James Ketter
(74) *Attorney, Agent, or Firm*—Townsend and Townsend and Crew LLP

(57) ABSTRACT

This invention relates to functional gene arrays of yeast. Novel aspects include the individual yeast cells, methods for making the yeast and the arrays, the arrays and uses for the arrays. A diploid bearing special genetic properties has been constructed to facilitate cloning of heterologous genes capable of providing essential functions. A selection method, using this strain allows the identification haploid yeast strains dependent for life on heterologous essential genes. The arrays of these strains comprise a library of unique members where each member is dependent for survival on the function of a heterologous gene complementing a different essential host gene which has been inactivated by the insertion of a dominant selectable marker. These arrays provide screening platforms for agents that specifically target the activity of these heterologous genes.

41 Claims, 3 Drawing Sheets

FUNCTIONAL GENE ARRAY IN YEAST

FIELD OF THE INVENTION

This invention relates to functional gene arrays of yeast. Novel aspects include the individual yeast cells, methods for making the yeast and the arrays, the arrays and uses for the arrays. A diploid bearing special genetic properties has been constructed to facilitate cloning of heterologous genes capable of providing essential functions. A selection method, using this strain allows the identification of haploid yeast strains dependent for life on heterologous essential genes. The arrays of these strains comprise a library of unique members where each member is dependent for survival on the function of a heterologous gene complementing a different essential host gene which has been inactivated by the insertion of a dominant selectable marker. These arrays provide screening platforms for agents that specifically target the activity of these heterologous genes.

BACKGROUND OF THE INVENTION

The understanding of the interaction of extraneous molecules with the machinery of a living cell is a central topic for all science and industrial activities where one desires to effect a change on a biological system by treatment with a chemical. This includes basic cellular research, pharmaceutical discovery, toxicology, agricultural sciences and environmental testing. The interaction can be studied at several levels of intricacy, however one is usually interested in relating the gross effect on a biological system with the molecular interactions that cause the effect. The usual mode of approaching this problem has been to identify a chemical that has an affect on an organism, then find the cellular molecule with which the chemical interacts. Alternatively, one can isolate cellular molecules, find chemicals that interact with them either by measuring binding of the two or by measuring a change in the function of the cellular molecule by the chemical. The chemical is then tested for its affect on the cell or organism as a whole. In an industry where discovery of the biological effect of chemicals at the molecular level is central to the discovery of useful compounds, the process of identifying biologically active compounds and their cellular "targets", becomes a key economic factor. Systems, materials and techniques that increase the efficiency of this process are useful and valuable.

The development of new techniques of measuring interaction between chemicals and biological molecules such as proteins, nucleic acids and membrane lipids has lead to the application of systems with the capacity for assaying many reactions simultaneously. These systems, referred to as high through put (HTP) systems, although automated and rapid, still demand either choosing the type of assay based on the known characteristics of the cellular target, or isolating the cellular target so that a physical interaction between the target and the chemical compound can be measured. Here we disclose a genetic system for generating ordered arrays of hundreds of functional cellular targets which can be used to assay the biological activities of large numbers of chemical compounds, with no prior understanding of the function of the chemical compound, nor prior choice of type of target to be assayed. The system can be used to both determine if a compound has an activity against one of the targets and identify the target.

The genetic system employs the yeast, *Saccharomyces cerevisiae*. The genetics of the organism are better understood than any other eukaryote and it is relatively easily manipulated genetically. The organism can grow either as a diploid with 16 pairs of homologous chromosomes, or after undergoing sporulation, as a haploid having only one member of each chromosome pair.

*Saccharomyces cerevisiae* has long served as a useful model for the analysis of eukaryotic gene expression and as a system to study the function of genes isolated from other organisms (heterologous genes) since yeast can be efficiently transformed by DNA molecules consisting of circular or linear plasmids carrying foreign genes under the control of a yeast transcription promoter. In some cases the protein product of the heterologous gene can functionally replace a missing or mutated yeast protein. This type of functional complementation has been used to identify and study genes from more complex organisms, such as higher plants and humans, since yeast can be much more easily grown than higher organisms or their cells. However, it requires that the yeast be made dependent on the foreign gene to grow. Current methods to do this are tedious and require cloning of the yeast gene to be replaced, as well as a complex selection procedure.

The elucidation of the function of many yeast genes followed the completion of the nucleotide sequence in 1996. A systematic study in which each open reading frame (orf) is deleted and the growth the haploid yeast carrying the deletion is measured has thus far revealed that of the some 6200 genes about 20% appear to be essential for growth.

The present invention provides for construction of yeast strains in which selection for haploid cells containing inactivated essential genes allows the simultaneous selection of strains in which the inactivated essential gene is replaced by a heterologous gene which may support growth or other critical cell functions. This invention also provides for the construction of arrays of such strains in which each member of the array contains a heterologous gene upon which that strain is dependent. These arrays in turn serve as platforms for the identification of chemical compounds that affect the function of heterologous genes expressed by individual members of the array. The array is therefore a system that can be used for both determining if a chemical compound is biologically active and identifying the target of the activity.

SUMMARY OF THE INVENTION

This invention provides for a stable haploid population of yeast cells having at least two selecting markers and a recombinant plasmid where: (a) the first marker is a dominant selectable marker wherein said marker is recombinantly inserted into an essential yeast gene rendering that essential gene inactive; (b) the second marker is a defined haploid-selecting recessive marker; and (c) the recombinant plasmid comprises a functional gene that complements the essential gene inactivated by the dominant selectable marker. A preferred species of yeast is *Saccharomyces cerevisiae*. Preferred dominant selectable markers are selected from the group consisting of: KAN, LEU2, LYS2, URA3, TRP1, HIS3 and ADE2. The preferred defined haploid-selecting recessive (resistant) marker are those selectable markers having a corresponding dominant counter selectable (sensitive) allele in the parental diploid yeast. The recessive markers are preferably created by insertion, deletion or point mutation which result in recessive selectable phenotypes. The preferred haploid-selecting recessive markers are can1, cyh2-1, lys2, met15 and ura3. The preferred dominant counter selectable (sensitive) allele is a wild type allele selected from the group consisting of CAN1, CYH2, LYS2, MET15 and URA3. Using this method in a preferred manner one can create a haploid yeast population wherein the diploid population is less than one in 1,000,000. It is further preferred that the population carries a functional gene on the plasmid that is a heterologous gene from a non-*Saccharomyces cerevisiae* organism.

In an alternative preferred population of haploid yeast, the population has a multiplicity of different dominant selectable markers inserted into more than one gene. A second and different defined haploid-selecting recessive marker having a corresponding dominant counter selectable (sensitive) allele in the parental diploid yeast may also be used to ensure and maintain high levels of haploidy in the population.

In a preferred embodiment the populations of haploid yeast are arranged as an array of individual members where the members are stable haploid populations of yeast cells as defined above. The members of the array are also preferably further defined as above.

This invention further provides for a diploid population of yeast which serves as the parental strain giving rise to the haploid yeast. This population of diploid yeast cells has at least two recombinant insertions and is transformed by at least one recombinant plasmid where: (a) The first insertion is a dominant selectable marker said marker inserted into an essential yeast gene rendering that essential gene inactive; (b) the recombinant plasmid in the cells are not the same; and, (c) the second recombinant insertion is a single copy of a dominant counter selectable (sensitive) marker and is allelic to a corresponding haploid-selecting recessive marker in the parental diploid yeast. It is possible for the diploid yeast to have two haploid selecting recessive markers. The preferred markers are as defined above for the dominant selectable markers and the dominant counter selectable markers.

This invention further provides for diploid yeast cells having the following recombinant insertions: (a) a first insertion that is a dominant selectable marker said marker inserted into an essential yeast gene rendering that essential gene inactive; (b) a second recombinant insertion positioned within approximately 5 centimorgans of a centromere where the insertion is a single copy of a first dominant counter selectable marker that is allelic to a corresponding recessive selectable marker and; (c) a third recombinant mutation that is introduced to the native copies of the gene corresponding to the first dominant counter selectable marker and renders those loci recessive selectable markers. The third recombinant mutation is typically introduced into two native copies of the gene corresponding to the first dominant counter selectable marker. To create a more stable population and to lower the diploid background in a subsequent step, it is desirable to have a fourth recombinant insertion within approximately 5 centimorgans of a centromere of a different chromosome than that of the second recombinant insertion and that is a single copy of a second and different dominant counter selectable marker and a fifth recombinant mutation that is introduced into the native copies of the gene corresponding to the second dominant counter selectable marker, and renders those loci recessive selectable markers.

This invention further provides for a method of making the yeast populations described above. The methods include those for creating a diploid yeast population by the steps of:

(a) recombinantly altering the yeast cell to comprise a dominant selectable marker said marker inserted into an essential yeast gene rendering that essential gene inactive; (b) recombinantly altering the yeast cell to also comprise a recombinant insertion that is a single copy of a first dominant counter selectable marker that is allelic to a corresponding recessive selectable marker; (c) introducing a first set of recombinant mutations that renders all copies of the native genes corresponding to the dominant counter selectable marker as recessive selectable markers; and, (d) culturing the cells to yield a diploid yeast population. Preferred yeast and markers for use in this invention are as described above. The method may further comprise the steps of:

(i) recombinantly altering the yeast cell to comprise a second recombinant insertion that is a single copy of a second and different dominant counter selectable marker that is allelic to a corresponding recessive selectable marker and; (ii) introducing a second set of recombinant mutations that renders all copies of the native genes corresponding to the second dominant counter selectable marker as recessive selectable markers.

The invention further provides for a method of creating a population of recombinant haploid yeast strains where the population has an essential inactivated gene that is complemented by a non-native, heterologous gene, said method comprising: i. transforming a diploid yeast cell having (a) a first recombinant insertion that is a dominant selectable marker said marker inserted into an essential yeast gene rendering that essential gene inactive; and, (b) a second recombinant insertion that is a single copy of a first dominant counter selectable marker that is allelic to a corresponding recessive selectable marker; with a plasmid that has a gene that complements the essential gene; ii. inducing meiosis to create haploid cells; iii. culturing the yeast in a media that contains a selecting agent that selectively eliminates those cells bearing the dominant counter selectable marker; and iv. culturing the yeast in a media that contains a selecting agent that selectively eliminates those cells not having the dominant selectable marker. In a preferred method, the yeast further comprises a single copy of a second dominant counter selectable marker that is different than the first counter selectable marker and is allelic to a corresponding selectable marker that is recessive to the dominant counter selectable marker.

The above methods will also comprise the further step of arranging the yeast populations as an array of yeast populations where the dominant selectable marker is inserted into different essential yeast genes. The arrays are preferably arranged or addressed so that each different population is segregated into an identifiable location. The method described above can further comprise repeating steps i–iv with a second yeast cell with the proviso that the inactivated essential gene is not the same and where the two yeast populations are placed adjacent to each other to create an array. It is often preferred that the method include *Saccharomyces cerevisiae* and the essential gene is complemented by a heterologous non-*Saccharomyces cerevisiae* gene.

This invention further provides for a method of determining the gene encoding the target of a biologically active compound comprising the steps of:

(i) creating an array of stable haploid populations of yeast cells having at least two selecting markers and a recombinant plasmid where: (a) the first marker is a dominant selectable marker wherein said marker is recombinantly inserted into an essential yeast gene rendering that essential gene inactive; (b) the second marker is a defined haploid-selecting recessive marker; and (c) the recombinant plasmid comprises a functional heterologous gene which encodes a gene product which complements the essential gene inactivated by the dominant selectable marker; where populations within the array are dependent upon different heterologous genes for survival; (ii) contacting the array with the biologically active compound in an amount that produces a compound-specific reaction with a population of the array but not with all populations and, (iii). determining the yeast population within the array that is reactive with the compound. In some instances, the dominant selectable marker is recombinantly inserted into more than one (different) essential yeast genes. The markers are as described above.

DEFINITIONS

Figure 1:
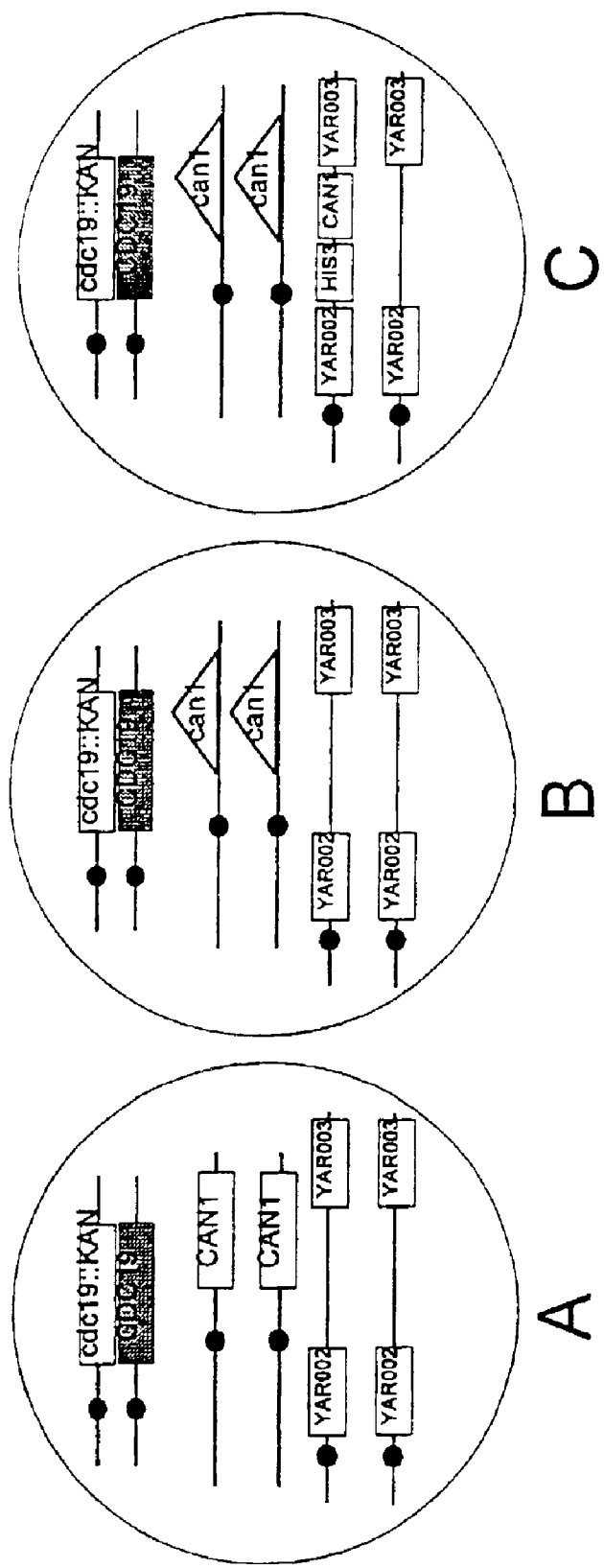
FIGS. 1., A, B., and C. Diagram of the genetic construction of a strain of the Acceptor Array.

"Allele" refers to one of two or more forms of a gene that may exist at a specific gene locus.

"Array" refers to a physical or spatial arrangement of yeast populations where the populations are unique and addressable as to location and/or genetic makeup.

"Complements" in the context of a gene refers to a gene that has the facility to replace the function of an inactivated gene which would otherwise produce a gene product that has a similar function to the protein being produced by the complementing gene. Because this is determined by survival or phenotype, the mechanism of function need not be identical. More specifically, an essential gene that has been inactivated can be complemented by a heterologous gene that can either produce a protein homologous to the protein encoded by the inactivated gene or a protein that provides a phenotype that permits survival (phenotype) by an second mechanism such as initiating a metabolic cascade which produces a product analogous to the inactivated gene's product.

"Counter selectable marker" refers to a selecting marker that distinguishes between a population bearing the marker and those without the marker by rendering those with the marker less viable or vigorous than those with the marker when a defined or specific agent (e.g. toxin) is present in the environment or defined condition is present in the environment (e.g. temperature). The marker can be an addition, a substitution or an insertion to a genome which is either adding non-functional nucleic acid to an existing gene or the addition of an intact heterologous gene. The marker can also be a deletion to an existing gene.

"Defined markers" refer to a selecting marker for which one understands and knows the conditions which permit it to be used as a counter selectable or as a selectable marker.

"Dominant Selectable Marker" refers to a marker that controls the phenotype of the organism having that marker.

"Essential yeast gene" refers to a gene, which is necessary for cell viability in a given culture media or environ. This includes situations where a multiplicity of defined mutations have been introduced to genes that render the elimination of single gene lethal where in the native or wildtype genome the elimination of that single gene would not be a lethal event. In other words as a result of the multiple mutations, a nonessential gene has become essential.

"Functional gene" refers to a gene which produces a gene product which carries out a definable function.

"Gene product" refers to either the nucleic acid transcription product of the gene coding sequence or the protein translation product of the gene coding sequence "Haploid" refers to a genetic state where there is one copy of each chromosome.

"Haploid-selecting recessive selectable marker" is a selectable marker that is used to select for a population of yeast in a haploid state by virtue of the marker inherently having a counterpart allele or gene which is a dominant counter selectable marker. The dominant counter selectable marker being used to remove all diploid forms of the yeast.

"Heterologous" refers to a functional non-native gene introduced into yeast cells by recombinant means.

"Locus" refers to a specific place on a chromosome (the genetic or physical position of a gene on a chromosome).

"Operably linked" refers to the placement of two defined elements in a manner in which they interact to produce a result. In the context of a promoter and a gene, they are operably linked when the promoter is positioned to permit a host cell to express the gene; i.e., the promoter is able to "drive" the gene.

"Parental diploid yeast" means the parent strains of yeast from which the haploid population was generated following meiosis.

"Population of yeast cells" refers to a multiplicity of yeast cells all having the same or identical defined genetic markers such as a select strain of yeast.

"Recessive Selectable Marker" refers to a gene whose phenotype is only expressed in homozygous diploids or in haploids and permits growth under defined condition and is not expressed in the presence of the dominant allele.

"Recombinant plasmid" refers to a novel DNA sequence formed in the laboratory using molecular biological techniques which may be introduced into a biological organism "Recombinantly introduced markers" refers to any man made alteration in the genome of a cell that is deliberate and defined.

"Selectable Marker" refers to refers to a selecting marker that distinguishes between a population bearing the marker and those without the marker by rendering those without the marker less viable or vigorous than those with the marker when an defined or specific agent (e.g. toxin) is present in the environment or defined condition is present in the environment (e.g. temperature). The selectable marker can be a deletion, substitution or an insertion to a genome which is either adding non-functional nucleic acid to an existing gene or the addition of an intact heterologous gene.

"Selecting agents" refers to agent (e.g. toxin or nutrient) that when added to or specifically deleted from a growth media selects for or against a specific sub-population of organisms.

"Selecting marker" refers to either a selectable or a counter selectable marker.

"Stable haploid population" means a population or culture of haploids that maintains the haploid state for repeat generations and does not without intervention from man revert to diploidy. It being recognized that the population does not exist without its culture media which must play a role in maintaining a viable state.

"Starter strain" refers to a diploid yeast strain containing a dominant selectable marker (e.g. KAN), interrupting one allele of an essential gene, from which the corresponding member of the Acceptor Array is made.

DETAILED DESCRIPTION

A. Introduction.

This invention provides a means to generate a novel array of haploid yeast strains designated a "Target Array." Each strain contains a heterologous gene that complements a defined yeast gene that has been disrupted so that without the foreign gene, the yeast would be unable to grow or perform a function for survival. The array provides a novel and useful method of assaying compounds to identify those whose activity is specific to the gene product of one of the heterologous genes.

The Target Array arises from a diploid "Acceptor Array" where each member contains an insertion of a dominant selectable marker into one allele of an essential gene rendering that copy of the essential gene non-functional. The Acceptor Array is constructed to contain genetic markers configured to allow for selective growth of haploid "daughter" progeny of the strains of the diploid Acceptor Array which contain the interrupted allele of the essential gene, but not the normal allele. Therefore the daughters can grow only if the function of the interrupted allele is supplied on a plasmid or other DNA vector (for example, a virus, phage or phagemid) containing a functional gene expressing a product that replaces the function of the essential gene.

The genetic markers of the Acceptor Array of this invention include a first dominant counter-selectable marker and a first recessive selectable marker, as well as a second dominant counter-selectable marker and a second recessive selectable marker.

The functional genes supplying the replacement functions are heterologous genes. They can come from any species and are cloned as an expression library using their own promoters or one provided on the vector.

The Target Array provides a novel approach to high through-put compound screening by contacting the strains of the Target Array with chemical compounds and observing the affect on growth or other observable parameters. Using a Target Array of several hundred strains, each dependent on a different heterologous gene to survive, it is possible to screen for biologically active compounds and their physiological/pharmacological targets. If a compound affects the growth or other physiological parameter of one or a few strains of the array, it is a candidate for having an activity specific for the product of the heterologous gene in the affected strain(s). Thus, the invention provides for a novel approach to screen large numbers of compounds for activity against an array of several hundred targets. The invention provides for a simple screening mechanism with a massively broad target scope which is heretofore unavailable.

This invention can in principle be carried out using either *Schizosaccharomyces pombe* or *Saccharomyces cerevisiae*; however, S. *cerevisiae* is preferred because it is readily available, its genome is well characterized, genetic methodologies are well established and culturing conditions are well known. Unless otherwise stated all methods described herein follow the protocols detailed in Adams, A., D. E. Gottschling, C. A. Kaiser and T. Stearns. 1998. Methods in yeast genetics. Cold Spring Harbor Laboratory Press, Cold Spring Harbor. In general, transformations will use a LiCl protocol. There are many appropriate media to grow or maintain yeast, conditions such as the reactivity or solubility of the compound to be tested may dictate the type of medium used. Useful growth media include YPD, YEPD or synthetic defined media. The cultures are serially maintained at about 30C.

B. Obtaining Recessively Selected, Essentially Complemented Haploid [RSECH] Yeast.

To construct the Target Array, one begins with starting diploid strains that are homozygous for all genes except those noted below. Most notably, each bears a heterozygous deletion of, or insertion into a specific essential gene such that one allele of the essential gene is rendered inactive. The diploid yeast strains that can be used as starting materials are not critical and can be obtained from the ATCC. In general one uses a strain such as W303 (ATCC#208352) or SKI (ATCC #204709) which is able to efficiently undergo meiosis. Alternatively one can obtain diploid yeast having known essential genes deleted by a dominant selectable marker from (for example) Research Genetics, (Huntsville, Ala.). FIGS. 1A–C provides a schematic overview of the creation of the diploid strains used in this invention.

Additional mutations are then recombinantly introduced into the starter diploid strain. The purpose of these additional mutations is to create or insert markers that permit the selection of haploid strains containing the inactive allele (i.e. the loss of the normal allele) of the essential gene such that the haploid strain is dependent upon an exogenous gene cloned on a extrachromosomal plasmid or other vector for growth. These markers comprise at least a first dominant counter-selectable marker and a first recessive selectable marker, such that only cells that have lost the counter-selectable marker, retained the recessive selectable marker, the first dominant selectable marker (i.e. the marker that interrupted the essential gene) and have received a cloned gene on a plasmid that provides the essential function, can grow.

Figure 2:
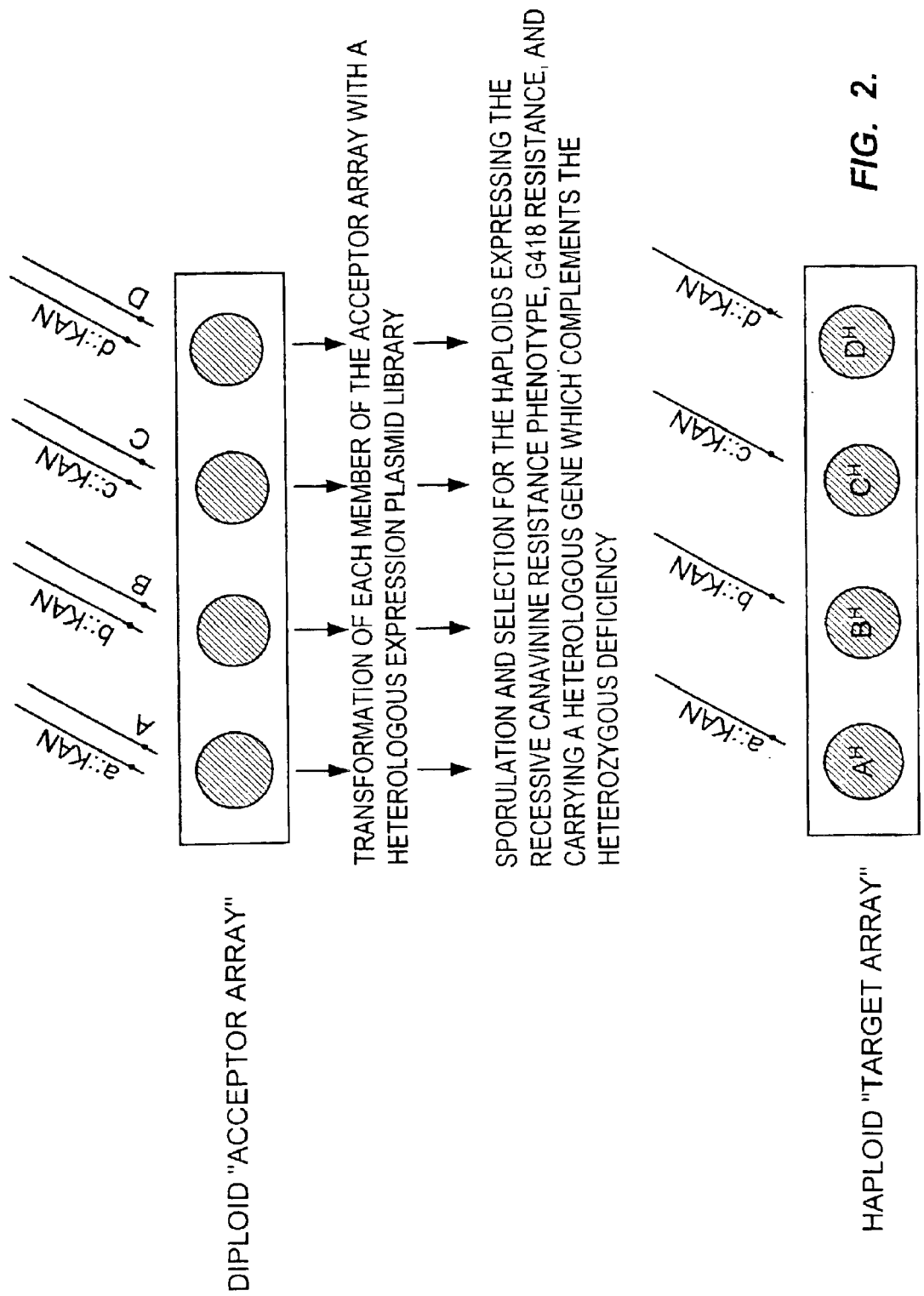
FIG. 2. Diagram of the transformation of the Acceptor Array with an Expression Library of Genes from a heterologous organism and induction of sporulation to generate a Target Array.

The term "essential gene(s)" include three types. Strains of diploid yeast (Acceptor Strains) carrying any of the four categories can be incorporated into the basic Acceptor Arrays (FIG. 2). Those genes that are known to be essentially defined (For example see, Winzeler, E. A., et al *Science* 285;901–906 August 1999) are the first type. Genes necessary for growth under specific conditions, different from the normal growth conditions comprise a second type of essential gene. Strains carrying interruptions in such genes may be unable to grow, for example, at elevated temperature or in the absence of externally added nutrients. Selecting for complementing heterologous genes (i.e. the gene providing the replacement function) is performed under the restrictive condition. Strains carrying heterozygous conditional lethal deficiencies can be incorporated into the Acceptor Array. A third type of essential gene is one that provides an essential function to a cell containing multiple gene disruptions such that the combination of mutations renders at least one of the genes essential for survival under defined conditions. Strains that carry a disruption of one copy of each of multiple genes, which together render the haploid receiving each of the mutant alleles, but none of the wild type alleles, unable to survive but which can be complemented by a heterologous gene can be incorporated into the Acceptor Array. Alternatively, the diploid in the acceptor array can contain homozygous interruptions in members of a group of genes that comprise an essential group of genes, and a heterozygous interruption (i.e. insertion of a dominant selectable marker) in one member such that the diploid can survive and be maintained, but none of the haploid progeny would survive unless a heterologous gene supplying one of the functions of the inactivated genes was supplied.

Selectable Markers for Use in RSECH Yeast.

Three types of markers are used, dominant selectable, dominant counter selectable and recessive haploid selecting markers.

Dominant selectable markers are known. The ones described below are preferred. Those of skill in the art will recognize that in the descriptions below, the conditions of use of each marker (selection conditions) are of necessity unique to that marker. Other markers would dictate other conditions of use. Although the markers and conditions described below are preferred, a skilled practitioner will recognize that other markers and conditions would satisfy the basic requirements.

The dominant selectable markers are used in this invention to select for inactivation of one of the two alleles of an essential gene in diploid yeast by recombinant insertion of the marker and by subsequent selection for the marker. Such heterozygous (diploid) yeast survive because they retain a functional copy of the essential gene. Following meiosis haploid cells containing the dominant selectable marker thereby also contain the inactivated allele. Dominant selectable markers include wildtype LEU2, URA3, MET15 and KAN$^r$ and his5 of *Schizosaccharomyces pombe* which complements his3 of *Saccharomyces cerevisiae*.

There are also a variety of different genes that can serve as dominant counter selectable markers. The basic requirement is that cells containing the marker do not survive or grow under the counter selecting conditions. The markers described below are the preferred ones for this procedure. Dominant counter selectable markers include CAN1 (Ono BI, Ishino Y, Shinoda S., *J Bacteriol* 1983 June; 154 (3):1476–9, "Nonsense mutations in the can1 locus of *Saccharomyces cerevisiae*") and CYH2 (Struhl K., Gene 1993 December; 26(2–3):231–41, "Direct selection for gene replacement events in yeast."), which confer sensitivity to the arginine analog canavanine and cycloheximide respectively. The respective mutant recessive alleles, can1 and cyh2-1 (Kaufer N F, Fried H M, Schwindinger WF, Jasin M, Warner J R., *Nucleic Acids Res* 1983 May 25;11(10): 3123–35. "Cycloheximide resistance in yeast: the gene and its protein.") are not sensitive to canavanine or cycloheximide. Heterozygous, diploid strains containing CAN1/can1 and CYH2/cyh2-1 or homozygotes containing CYH2 or CAN1 do not grow in the presence of canavanine and or cycloheximide. However, haploids containing the recessive selectable alleles can1 and cyh2-1, homozygous can1/can1 and/or cyh2-1/cyh2-1 diploids are resistant to canavanine and/or cycloheximide.

Other dominant counter selectable/recessive selectable pairs exist and could be used in the selection for haploids. For example, MET15 conferring sensitivity to methyl mercury in MET15 haploids and MET15/met15 heterozygous diploids, and LYS2 which confers sensitivity to alpha amino adipate in LYS2 haploids and LYS2/lys2 heterozygotes.

For recessive selectable markers, the basic requirement is that the recessive selectable gene have a dominant sensitive allele or counterpart, the basic properties of which are described above. The markers described below are the preferred ones. The can1 and cyh2-1 recessive haploid selecting markers are described above. Two other genes that can be used are the met15 allele which confers resistance to methyl mercury in met15 haploids and lys2 which confers resistance to alpha amino adipate in lys2 haploids.

Optionally two other methods may be employed to enrich for haploid yeast. First, one may enrich for the complemented haploid population by including a second dominant selectable marker whose expression is driven from a haploid specific promoter (one repressed by α1/α2). This second dominant selectable marker is preferentially included on the recombinant library plasmid that also carries the complementing gene but may also be inserted into a chromosome. The dominant selectable markers include those described previously. The haploid specific promoter may be derived from haploid specific genes including MATα1, MATα2, RME1, STE4, STE5, STE12, STE18, FUS1, SCG1, Ty1, and HO (Herskowitz, I., J. Rine and J. Strathern. 1992. Mating-type determination and interconversion. In *The Molecular and Cellular Biology of the Yeast Saccharomyces* (ed. E. W. Jones, J. R. Pringle and J. R. Broach). Cold Spring Harbor Laboratory Press, Cold Spring Harbor, N.Y.). A second optional method for enriching for haploids is to treat sporulated cultures with zymolyase which preferentially leads to lysis of vegetative cells but not spores (Herman P K and J. Rine. 1997. Yeast spore germination: a requirement for Ras protein activity during re-entry into the cell cycle. EMBO J. 16 (20):6171–81.).

Creation of the Acceptor Array.

The members of the Acceptor Array (FIG. 2) have previously characterized essential genes rendered nonfunctional as well as essential genes of unknown function rendered non-functional. The identity of essential yeast genes can be conveniently determined from the literature, i.e., the *Saccharomyces* Genome Database and the *Saccharomyces* Gene Deletion Project. The complete yeast genome has been sequenced and has been shown to contain approximately 6200 open reading frames (Goffeau, A., B. G. Barrell, H. Bussey, R. W. Davis, B. Dujon, H. Feldmann, F. Galibert, J. D. Hoheisel, C. Jacq, M. Johnston, E. J. Louis, H. W. Mewes, Y. Murakami, P. Philippsen, H. Tettelin and S. G. Oliver. 1999 *Science* 274, 546–552. Life with 6000 genes.) Thus far about 20% of the genes tested have been shown to be essential. An essential gene being any gene which if inactivated in a haploid yeast strain leads to cell death or cessation of growth. Essential genes can be empirically determined also.

Beginning with the starter diploid strain described above, heterozygous interruptions are introduced into known essential genes or genes that are in combination essential. The preferred method for introducing the dominant selectable marker into an essential gene is a PCR based gene deletion procedure which is described in more detail below. One of reasonable skill will also recognize that other methods could be used. These could include, but are not limited to methods which involve first cloning the essential yeast gene in bacteria then using molecular biological techniques to mutate the gene in bacteria followed by replacement of the native yeast gene with the mutated copy. Alternatively could use a Cre-Lox based system (Guldener U, Heck S, Fielder T, Beinhauer J, Hegemann JH., *Nucleic Acids Res* 1996 July 1;24(13):2519–24, "A new efficient gene disruption cassette for repeated use in budding yeast.") to excise a disruption cassette from a plasmid transformed into yeast which would then integrate into, and disrupt a targeted gene by homologous recombination. One of skill in the art will also recognize that each of these methods would necessitate the construction of specific plasmids and in all cases a particular plasmid would be specific to a given essential yeast gene disruption.

Once the yeast are transformed, the successful transformants are selected for by growing on a selectable media specific for the dominant marker, e.g. methotrexate for dhfr and G4148 for kanamycin resistance. The collection of diploid strains each carrying a heterozygous lethal deficiency in a different gene constitutes the Acceptor Array.

Disruption of Essential Yeast Genes with a Dominant Selectable Marker.

The polymerase chain reaction (PCR) based gene replacement protocol (Guldener U, Heck S, Fielder T, Beinhauer J, Hegemann J H., *Nucleic Acids Res* 1996 Jul. 1;24(13): 2519–24, "A new efficient gene disruption cassette for repeated use in budding yeast.") can be used to eliminate one allele of each of the genes fitting the criteria outlined above. In most instances one copy of the gene of interest is replaced or interrupted in the diploid Starter Strain with a Kanamycin (KAN$^r$) resistance gene. The KAN resistance cassette is generated by PCR using gene specific oligonucleotide primers. In cases in which multiple disruptions are performed, additional selectable markers are used (LEU2, URA3, his5 of Schizosaccharomyces pombe which complements his3). In each case, a linear DNA fragment consisting of the KAN$^r$ gene flanked by target gene specific sequences is introduced into the cells by conventional cell transformation methods. As a result of homologous recombination between the target gene and the target gene specific sequences flanking the KAN$^r$ gene the DNA fragment is integrated into the chromosome disrupting or displacing one allele of the targeted gene.

Transformants are selected based on G418 resistance conferred by KAN$^r$ expression from the target gene locus. Rare cells in which both target alleles are displaced die since they lack the essential function. Non-transformed cells also die since they do not express G418 resistance. Only those cells carrying a heterozygous deficiency of the essential gene survive the selection protocol.

Once the dominant selectable marker is inserted into an essential gene, it is necessary to introduce the haploid selecting recessive markers. These markers are used to select for yeast that successfully complete meiosis and are thus haploid. The can1 and cyh2-1 markers described above which confer resistance to canavanine and cycloheximide respectively, fall into this category of selectable marker. Because they are recessive, their respective resistance phenotypes are only seen in can1 and cyh2-1, or can1; cyh2-1 haploid yeast or in the corresponding homozygous diploids. Although can1 and cyh2-1 are the preferred markers it is understood that several other genes can serve as haploid selecting recessive markers including met15, lys2 and trp1 which confer resistance to methyl mercury, alpha amino adipate and 5-fluoroanthranilic acid respectively.

Generally, the recessive markers are generated by inactivation of both wildtype (dominant) alleles. This permits the newly generated recessive marker to express its phenotype and function. There are different routine ways of introducing these markers into a yeast. Either a diploid or haploid strain can be used.

If a diploid strain is used as a starting strain, one can use homologous recombination to target a gene its corresponding dominant markers for replacement or disruption and subsequently select for homozygotes of the inactivated gene by selecting for cells that grow in the presence of the counterselecting agent. These homozygotes arise spontaneously as a result of mitotic recombination. The chosen marker such as URA3 should act as both a selectable and a counterselectable marker to permit one to first select for and then eliminate that marker in a subsequent selection step. To increase the rate of mitotic recombination, one can optionally flank the marker with direct repeats which promote mitotic recombination. The preferred direct repeats are from the hisG repeats of Salmonella.

To exemplify the first method of introducing the recessive selectable marker, we use the CAN1 genes (FIG. 1B). In the absence of the dominant, wildtype CAN1 genes, the yeast are resistant to canavanine because it can not be transported into the cell. Eliminating the two CAN1 loci in the diploid starter strain creates a strain that is homozygous can1Δ/can1Δ, and thus canavanine resistant. To do this, a plasmid was constructed bearing an insertion of the URA3 selectable marker flanked by hisG repeats of Salmonella into the sequences flanking CAN1, such that the CAN1 open reading frame is deleted. This plasmid serves as a source of DNA that is used in a one step gene replacement to replace one CAN1 allele with URA3 by recombination of the remaining CAN1 sequences with one of the chromosomal copies of CAN1. The presence of the inserted selectable URA3 marker allows selection of the Ura$^+$ transformants.

The URA3 insertion is removed by selecting at this stage for 5-FOA resistant derivatives that have experienced recombination between hisG repeats to remove the URA3 gene yielding can1Δ; CAN1 yeast. Yeast homozygous for can1Δ, are selected by plating on media containing canavanine. The only yeast that can grow on this medium are those which have "homozygosed" the can1 loci to can1Δ/can1Δ. These yeast express the recessive Can$^r$ phenotype because both dominant wildtype CAN1 alleles have been deleted.

A second method for introducing recessive markers uses haploids as starting strains. This method can be exemplified using cycloheximide resistance for which expression of the recessive cyh2-1 allele is required. To obtain cycloheximide resistant yeast, the wildtype allele, CYH2, must be replaced by the mutant allele because it is dominant. To accomplish this a DNA fragment containing the cyh2-1 allele along with the 5' and 3' flanking regions is used to transform two haploid yeast strains, replacing the wildtype CYH2 allele with cyh2-1. Transformants are selected based on their resistance to cycloheximide, which is conferred by the cyh2-1 mutant allele. Since the wild type CYH2 allele is dominant and confers sensitivity to cycloheximide, only those transformants that have both lost the dominant wild type allele and incorporated the mutant cyh2-1 allele will survive the selection.

The two haploid strains are then mated, creating diploid yeast that are homozygous cyh2-1/cyh2-1 and consequently cycloheximide resistant.

After the recessive marker is in place, it is necessary to introduce dominant counter selectable markers into the diploid yeast. It is preferred that the dominant counter selectable marker be inserted into a region near the centromere (FIG. 1C). The function of the dominant counter selectable markers is to confer sensitivity to specific selective agents that are used to specifically eliminate the population of cells expressing the counter selectable marker. This marker allows for the elimination of contaminating diploids from the desired haploid yeast population generated by meiosis.

To increase the efficiency of the counter selection and hence lower the number of contaminating diploids, it is desirable to move the dominant counter selectable marker from its native locus (when a corresponding allele exists) to a position near a chromosomal centromere. This decreases the frequency of loss of the marker by mitotic recombination between the marker and other regions of the chromosome and thereby reduces the backgrounds of contaminating diploids following meiosis.

Although the text below describes moving the CAN1 or CYH2 dominant counter selectable markers near the Chromosome IV centromere, it is understood that the markers could be placed near the centromere of any of the sixteen yeast chromosomes. An optional enrichment against (disomic) haploids that have inherited a copy of the chromosome with the disrupted essential gene and also its homolog with the functional copy of the essential gene can be achieved by placing the dominant counter selectable marker adjacent to the centromere of the same chromosome that bears a dominant selectable marker in one copy of an essential gene. For example the markers could be inserted into the region between the Chromosome I centromere and the 5' end of the non-essential ORF YAR002w, or between the 3' end of the non-essential ORF YAL001c and Chromosome II centromere, or between the Chromosome III centromere and the 5' end of the non-essential ORF YCR001w. One reasonable skilled in the art will recognize that in the description below the conditions are specific to insertion of the dominant counter selectable markers near the Chromosome IV centromere and that insertion of the markers near the centromeres of other chromosomes would necessitate the use of other targeting sequences. A skilled practitioner will also recognize that placement of the marker near any of the yeast centromeres will lead to the desired reduction in the frequency of mitotic recombination.

Because the native CAN1 and CYH2 loci are considerable distances from their respective centromeres, homozygosis, by recombination between the mutant allele-sand the wildtype alleles can result in loss of the counter selectable marker allowing the generation of canavanine or cycloheximide resistant diploid cells. These diploid cells would still contain one wildtype allele of the essential gene and therefore not be dependent on the corresponding heterologous gene. This recombination, followed by segregation of chromatids bearing like alleles to the same daughter cells, (homozygosis), occurs at a frequency approaching 1 in $10^5$. It is important to have a low background so that rare cDNAs (those present at less than 1 in $10^5$ plasmids) can be cloned from the plasmid library and selected by complementation of the inactivated essential gene. To reduce the frequency of recombination between the centromere and the dominant counter selectable marker, and thus the frequency of homozygous CAN1 and/or CYH2 diploids following meiosis, the starting diploid strain bears a single copy of the dominant counter selectable marker adjacent to a centromere.

Wildtype CAN1 is inserted at the TRP locus of chromosome IV, adjacent to the centromere by homologous recombination between the TRP locus and TRP DNA sequences flanking CAN1 on the linear DNA fragment used for transformation. This reduces the incidence of $Can^r$ diploids to less than 1 in $10^6$ after the diploid yeast complete meiosis. Similarly, to reduce the frequency of recombination between the CYH2 dominant counter selectable marker and the centromere in subsequent meiotic assays CYH2 is placed in a position proximal to the chromosome VII centromere. To accomplish this the wildtype CYH2 allele is inserted between intergenic sequence linking the YGR001c and YGR002c yeast open reading by homologous recombination between a DNA fragment carrying CYH2 flanked by YGR001c to YGR002c intergenic sequence and the YGR001c to YGR002c intergenic sequence itself.

The diploid strains having the above genetic configuration represent the members of the Acceptor Array. The final steps described below, introduce the complementing plasmids and produce a haploid Target Array.

Construction of an Essential Gene Complementing [EGC] Plasmid Library.

The principle requirement of the EGC plasmid library is that the recombinant insert be expressed under the control of a regulated yeast promoter from a plasmid carrying a dominant selectable yeast marker such as, but not limited to, LEU2 or URA3. Our preferred plasmid vector is pBM272 described in Johnston, M. and Davis, R. W. *Mol. Cell. Biol.* 4, 1440–1448 (1984) "Sequences that regulate the divergent GAL1-GAL10 promoter in *Saccharomyces cerevisi.*" Plasmid BM272 is a centromere-containing shuttle vector which carries the Gal1 promoter which is induced by the Gal4 gene product in the presence of galactose and also carries the URA3 dominant selectable marker. One skilled in the art will recognize that other plasmid vectors could be used as well. Also, although the text below describes the construction of recombinant cDNA libraries from polyadenylated RNA it is understood that recombinant libraries could also be constructed from total RNA or genomic DNA. One reasonably skilled in the art will recognize that the specific conditions used to construct the recombinant library will depend on the type of library being constructed.

In most cases the EGC plasmid library is constructed from poly A mRNA. The RNA may be isolated from different organisms or from different tissues or disease states of a particular organism. Messenger RNA is converted to double stranded cDNA by standard methods using RNA dependent Reverse Transcriptase and DNA polymerase. The cDNA is subsequently cloned into an *E. coli/S. cerevisiae* shuttle plasmid such as pBM272, which carries a URA3 selectable marker and places expression of the cloned cDNA under the control of the galactose inducible Gal1 promoter.

Optionally, for organisms that are closely related to *Saccharomyces cerevisiae* it is possible to use libraries of genomic DNA, relying on expression from the heterologous promoters.

Transformation of the Acceptor Array with the EGC Plasmid Library.

To identify recombinant plasmids carrying heterologous gene able to complement essential yeast genes the EGC plasmid libraries are introduced into diploid yeast by transformation. Although the lithium acetate protocol (Adams, A., D. E. Gottschling, C. A. Kaiser and T. Stearns. 1998. Methods in yeast genetics. Cold Spring Harbor Laboratory Press, Cold Spring Harbor) is the preferred method of transformation, those of skill will recognize that other methods of transformation such as, but not limited to, electroporation (Thompson J R, Register E, Curotto J, Kurtz M, Kelly R., Yeast 1998 April 30;14(6):565–71. An improved protocol for the preparation of yeast cells for transformation by electroporation.) may be used as well.

To identify EGC plasmids containing genes able to replace the function of each inactivated essential yeast gene, each yeast strain included in the Acceptor Array is individually transformed with the EGC plasmid library. Successfully transformed diploids are selected based on markers carried by the plasmids such as uracil prototrophy on minimal medium lacking uracil. A particular transformed diploid, now constitutes a mixture of yeast each carrying the same heterozygous lethal deficiency but different EGC plasmids. To identify the EGC plasmid able to complement a specific essential deficiency, the transformed diploid population is subjected to the meiotic assay described below.

Using the Selectable Markers to Isolate RSECH Yeast Containing the ECG Plasmid with the Heterologous Gene that Replaces the Inactivated Essential Gene.

To identify haploid yeast carrying plasmids expressing heterologous genes able to complement essential yeast genes a collection of selectable markers is used. These markers include the dominant selectable marker used to inactivate the essential yeast gene, the haploid selecting recessive marker used to select for haploid yeast and the library plasmid expressing the heterologous gene able to complement the essential yeast gene.

Isolating from a transformed yeast population those cells harboring plasmids able to complement a lethal deficiency requires a robust selection. The procedure used in this invention selects for cells which are 1) G418 resistant and thus carry the $KAN^r$ dominant selectable marker inserted into an essential yeast gene, 2) carry a library plasmid with a recombinant DNA insert capable of complementing the essential yeast gene, and 3) are canavanine resistant because they carry the haploid selecting recessive can1 deletion but not the CAN1 dominant counter selectable marker. To accomplish these goals, the transformed diploid yeast population is transferred to a medium that induces meiosis of yeast such as *S. cerevisiae*. The sporulated cultures are plated on medium containing canavanine, and G418 and lacking uracil, and containing galactose as a carbon source (and inducer of expression of the cDNA from the Gal1 promoter). To survive on this medium, cells must carry the KAN resistant dominant selectable marker inserted into and inactivating the essential yeast gene. They must also carry a recombinant gene able to complement to inactivated yeast missing essential gene. Lastly they must not carry the CAN1 locus which confers sensitivity to canavanine.

Diploids that have failed to sporulate will perish on this medium because they carry the CAN1 locus. Canavanine resistant spores can only survive on the medium if they also carry the KAN disruption of the essential yeast gene that confers resistance to the G418. However because these spores will not carry a functional version of the essential yeast gene, they also will perish unless they carry a recombinant cDNA that complements this defect. Assorted events can yield cells that survive on the final medium without a complementing plasmid. These can be distinguished from complemented survivors because those that carry a complementing plasmid can not live without it.

Dependence upon the complementing gene can be tested by plating on 5-FOA which selects against the library plasmid because it carried a URA3 marker and glucose dependent inhibition of growth, because the plasmid borne cDNA is expressed from the Gal1 promoter which is suppressed by glucose.

Uses of the Invention.

Figure 3:
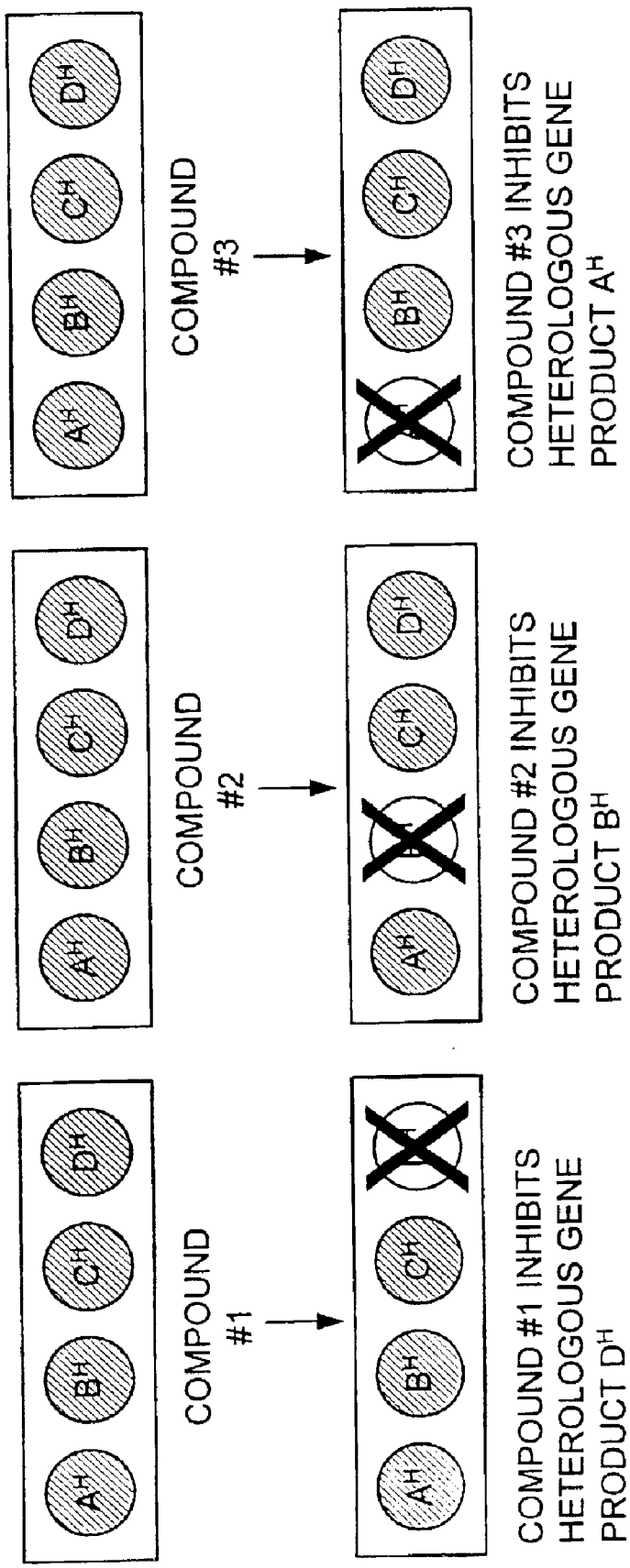
FIG. 3. Diagram of the use of a Target Array to identify biologically compound and their targets.

Collections of haploid cells bearing the essential complementing heterologous genes constitute "Target Arrays". Because of the methodologies used in this invention, these Target Arrays are comprised of sets of isogenic haploid strains that vary only in the identity of the heterologous gene upon which they depend for their survival. Consequently these arrays have utility as platforms for screening the effects of various chemical agents against the function of the heterologous genes. An agent that specifically affects the function of a particular heterologous gene only affects the growth of the one strain in the collection that depends upon that gene. Methods for testing drug sensitivities of microorganisms on nutrient agar or liquid media containing test compounds are well established (FIG. 3).

Generally yeast strains on agar plates or in liquid media are placed under appropriate growth conditions, usually 30° C. and the growth of the yeast (rate of colony formation on agar plates or increased cell density in liquid media) is monitored by visual inspection or by automated densimetric analysis (ref to instruments). Growth of individual strains are compared between samples containing a test compound and control samples with no test compound. The affect of a compound can be positive or negative. If the effect is positive colonies (cells) growing in the presence of the compound grow faster than the corresponding control sample growing in the absence of the test compound. If the affect is negative, it is reasonable to conclude that growth is inhibited by the presence of the compound.

Compounds that affect the growth of one or a small number of strains are considered candidates for having specific action on the gene product of the foreign gene in each of the affected strain. Compounds which do not affect growth of any strain either have no activity on any of the gene products or are not able to penetrate the cell wall or membrane or are inactivated by a yeast function. Compounds affecting growth on all or nearly all of the strains of the array are considered active against one or more yeast gene products and hence, are not specific for a foreign gene product.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

Example 1

Creating an Array of Haploid Yeast Populations Carrying Human Genes Able to Complement Lethal Deficiencies In this example the starting diploid yeast strains carrying heterozygous lethal deficiencies were obtained from Research Genetics. The protocols outlined below describe the specific case in which human genes able to complement a lethal CDC19 deficiency in haploid yeast are identified. This specific case serves only as an example. There are currently 786 additional yeast strains carrying heterozygous lethal deficiencies available from Research Genetics. Each of these strains and each new strain as it becomes available will be subjected to the same analysis. The genotypes of the relevant parental strains are:

BY4741: MATα his3Δ1 leu2Δ0 met15Δ0 ura3Δ0
BY4742: MATα his3Δ1 leu2Δ0 lys2Δ0 ura3Δ0
BY4743 is made by mating BY4741 and BY4742.

Step 1. Creating of a Haploid Selecting Recessive Marker in Diploid Yeast Strains Carrying Heterozygous Lethal Deficiencies.

In this example the beginning diploid yeast strain carried a kanomycin gene (KAN) insertion into yeast open reading frame YAL038W that resulted in inactivation of one allele of the CDC19 gene (FIG. 1A). The CDC19 gene encodes Pyruvate Kinase. Since the CDC19 gene product is essential the cdc19::KAN gene knockout can only be maintained as a viable heterozygous diploid.

The goal of the genetic manipulations described here was to inactivate both alleles of the CAN1gene thus rendering the resulting yeast cell resistant to the toxic arginine analog canavanine (can$^r$). For the yeast cell to be Can$^r$ both wildtype CAN1 alleles must be inactivated since the wildtype canavanine sensitive phenotype is dominant. This was accomplished in three sequential steps:

Replacing a one Copy of CAN1 with a can1::hisG-URA3-hisG Cassette.

The CAN1 genes were deleted by first disrupting one allele with a can1::hisG-URA3-hisG-disruption fragment, then selecting Can$^r$ derivatives to identify those that became homozygous at this locus through mitotic recombination. The beginning diploid yeast was homozygous for a ura 3deletion mutation (ura3/ura3) and consequently was unable to grow unless uracil was included in the growth medium. By replacing CAN1 with URA3 the transformed cells gained the ability to grow in the absence of added uracil.

To accomplish this the diploid yeast were transformed with a can1::hisG-URA3-hisG disruption fragment isolated from plasmid pC1. The plasmid pC1 was constructed by first cloning a 2573 bp genomic DNA fragment containing the CAN1 gene and 400 bp of upstream and downstream flanking sequence into pBlueScribe, (Stratagene, La Jolla, Calif.). The resulting plasmid pBS:CAN1 was subsequently restricted with BamHI and SalI to remove the CAN1 coding sequence and the hisG::URA3::hisG fragment was cloned into the same sites yielding pC1. The can1::hisG-URA3-hisG fragment could be liberated from pC1 by restriction with BglII which cleaved at the termini of the 5' and 3' CAN1 flanking sequences.

The liberated BglII fragment was the disruption fragment for use in the diploid yeast and ws made up of the following nucleotide sequences. The 5' and 3' ends of the fragment carry 400 bp of homology to the DNA sequences immediately upstream and downstream of the CAN1 translation initiation and stop codons respectively. These sequences served to target the DNA fragment into the CAN1 locus, deleting the open reading frame. Immediately inside the targeting sequences were single copies of an approximately 1 kb interval containing the hisG repeats of Salmonella inverted repeats. The hisG repeats were included so that the newly introduced URA3 gene could be removed by recombination between the repeats in the second step of the procedure. This enables one to reuse the selectable URA3 marker in subsequent genetic manipulations as needed. The final element of the disruption fragment was the URA3 gene, which was bounded by the hisG repeats.

The CAN1 gene was deleted by first transforming the diploid yeast with the can1::hisG-URA3-hisG disruption fragment and selecting for uracil protrophy by plating the transformants on minimal media lacking uracil. Transformation of the yeast diploid was carried out using a standard lithium acetate protocol described in (Adams, A., D. E. Gottschling, C. A. Kaiser and T. Steams. 1998. Methods in yeast genetics. Cold Spring Harbor Laboratory Press, Cold Spring Harbor)
Eliminating the URA3 Insertion.

The presence of the direct hisG repeats flanking the URA3 gene in the can1::hisG-URA3-hisG cassette made it possible to identify derivatives that had lost the URA3 gene by recombination between the repeats (leaving behind a can1::hisG locus). Ura$^+$ transformants ($10^6$ cells) were plated on medium containing 5-floroacotic acid (5-FOA), to select for FOA resistant derivatives that had experienced recombination between hisG repeats to remove the URA3 gene. Cells expressing URA3 were sensitive to 5-FOA and thus killed.

(a) Isolating Derivatives that were Homozygous for the can1::hisG Allele.

To select for a deletion of the remaining CAN1 allele, $10^6$ 5-FOA resistant yeast were plated on canavanine medium (Adams, A., D. E. Gottschling, C. A. Kaiser and T. Steams. 1998. Methods in yeast genetics. Cold Spring Harbor Laboratory Press, Cold Spring Harbor). All yeast cells expressing the remaining CAN1 allele were killed under these selective conditions. The only yeast cells able to survive this selection were the rare cells in which the strain had become homozygous, can1::hisG/can1::hisG, by mitotic recombination. Such strains arose at a frequency of about $10^{-4}$. Such cells are CAN1 null mutants and thus expressed the recessive canavanine resistant phenotype. (FIG. 1B)

Step 2. Creating a Dominant Counter Selectable Marker

To facilitate the meiotic complementation assay described below it was necessary that the starting diploid be further modified to carry a single copy of a dominant counter selectable marker, CAN1. To reduce the frequency of recombination between the dominant sensitive marker and the centromere in subsequent meiotic assays the CAN1 gene was placed in a position proximal to the chromosome 1 centromere. To accomplish this, a plasmid bearing the wildtype CAN1 allele and the HIS3 gene, both inserted within the intergenic region separating the YAR003 and YAR004 open reading frames on Chromosome I(pC2) was constructed as a source of a DNA fragment used to insert CAN1 adjacent to the centromere of Chromosome I. A linear DNA fragment bearing the YAR002::CAN1, HIS3::YAR003W construct was used to transform the diploid strain bearing the homozygous can1::his alleles following the published transformation protocol. (see Adams, A., D. E. Gottschling, C. A. Kaiser and T. Steams. 1998. Methods in yeast genetics. Cold Spring Harbor Laboratory Press, Cold Spring Harbor).

Transformants were identified by histidine prototrophy on minimal media lacking histidine. Transformants that had successfully inserted the YAR002Ca::CAN1, HIS 3::YAR003W cassette also became Can$^S$. The resulting Can$^S$ yeast thus carried a single copy of CAN1 which served as the dominant counter selectable marker (i.e. confers sensitivity to canavanine) and the double deletion of the native CAN1 loci which served as the haploid selecting recessive markers conferring resistance to canavanine. (FIG. 1C).

Step 3. Creating a Transformed Diploid Yeast Population.

The diploid yeast strain carrying the inactivated CDC19 gene as well as the haploid selecting recessive marker and the dominant counter selectable marker were transformed with a Human cDNA library constructed in the yeast plasmid Lambda Yes (American Type Culture Collection catalog number 87273) in which cDNA fragments were cloned behind a GAL1 promoter (Johnston, M. and Davis, R. W. Mol. Cell. Biol. 4, 1440–1448 (1984) "Sequences that regulate the divergent GAL1-GAL10 promoter in *Saccharomyces cerevisia*"). Transformation followed the published protocol, selecting for Ura$^+$ cells (the selectable marker on Lambda Yes). This third step resulted in the generation of a heterogeneous population of yeast carrying library plasmids with a variety of cDNA inserts. The selection scheme described below in Step 4 was designed to isolate from this heterogeneous yeast population, those transformed cells which harbored a plasmid carrying a Human cDNA able to complement the CDC19 deficiency.

Step 4. Creating a Complemented Haploid Yeast Population.

A robust selection was preferred to isolate those yeast cells which harbored plasmids able to complement the CDC19 deficiency from the entire transformed population generated above. This selection step selected for cells which (i) carried the KAN$^r$ dominant selectable marker inserted into yeast CDC19, (ii) carried a library plasmid with a recombinant DNA insert capable of complementing the cdc19::KAN gene, and (iii) did not carry the carry the dominant counter selected CAN1 marker. To accomplish these goals, the transformed diploid yeast population created as described in step 3 was transferred to a medium that induced meiosis of *S. cerevisiae*. The transformed cells were pooled, introduced in rich medium (YPD), at a density of $5 \times 10^6$ cells per milliliter. The culture was grown with aeration to $5 \times 10^7$ cells per milliliter at 30° C., then transferred to 1% potassium acetate and incubated for 48 hours at 27° C. with aeration.

The sporulated cultures were plated on medium containing complete medium containing canavanine, and G418 and lacking uracil, and containing galactose as a carbon source (and inducer of expression of the cDNA) at a density of $10^8$ cells per plate. Haploid cells that carried the KAN resistant dominant selectable marker (inserted into and inactivating the yeast cdc19 gene and conferring resistance to G418), a human gene able to complement the inactivated yeast CDC19 gene, and have lost the copy of the chromosome carrying the CAN1 locus (by virtue of meiotic segregation) survive on this medium.

Diploids that failed to sporulate perished on this medium because they carried the CAN1 locus. One half of spores did not carry this locus. Can$^r$ spores survived on the medium only if they also carried the cdc19::KAN locus, which conferred resistance to the G418. Because these G418 resistant spores did not carry the functional version of CDC19, they would also have perished unless they carried a cDNA that complemented this defect.

Optionally, to enhance the efficiency with which the contaminating unsporulated diploids were eliminated, a dominant selectable marker whose expression was driven by a haploid specific promoter could have been included on the cDNA library plasmid. Alternatively, enzymatic treatment of the sporulated culture with Zymolyase (ICN catalog number 32092) which selectively eliminates diploids by attacking the diploid cell wall could have been used to eliminate residual contaminating diploids from the sporulated culture to enhance the efficiency of the procedure.

Assorted events could yield cells that survived on the final medium without a complementing plasmid. Mitotic recombination between the centromere and CAN1 could yield homozygous Can$^r$ diploids that could survive on the final medium. Additionally, meiotic segregation errors could yield Can$^r$ hapolids that inherited both the cdc19::KAN and CDC19 bearing chromosomes. These could be distinguished from complemented survivors because those that carry a complementing plasmid could not live without it. Dependence upon the complementing gene was tested by plating on 5-FOA and growing on glucose, which would repress expression of the cDNA. Our results identified three pyruvate kinase genes from the human cDNA library.

Step 5. Creating an Array of Complemented East Populations.

An array of complemented yeast populations is created by repeating the steps detailed in step 1–4 starting with a different yeast cell carrying a heterozygous deficiency of a different essential yeast gene. The result of this step will be the generation of a spatially ordered array of complemented yeast strains each dependent on expression of a different Human cDNA for survival. (FIG. 2).

Example 2

Creating CD1, a Diploid Population Carrying Multiple Haploid Selecting Recessive and Dominant Counter Selectable Markers.

For specific genes, the BY4743 genetic background of the diploid strains obtained from Research Genetics is not ideal for the meiotic assay as described above in Step 4 of Example 1. In some cases it will be advantageous to begin with a different diploid strain (CD1) in which all of the requisite genetic features for performing the meiotic assay are in place. Situations in which CD1 rather than BY4743 is used include: genes within a short distance of the allele near the Chromosome IV centromere and construction of strains with multiple deletions of genes which lead to a lethal phenotype. If an inactivated essential gene is near the counter selectable CAN1 marker on Chromosome IV, the two genes will always segregate together during the meiotic assay, and canavinine resistance haploids will never carry the mutated essential gene. In these cases it will be necessary to either place the CAN1 allele on a different chromosome or include a second counter selectable marker.

Some essential functions are performed by collections of redundant genes. To clone heterologous genes that provide a complementing function, the meiotic assay is performed with a diploid deleted for multiple genes. Ultimately two modified haploid strains will be mated to create the diploid strain carrying two haploid selecting recessive markers and the two corresponding dominant counter selectable markers. The inclusion of the second set of haploid selecting recessive (Step 3: cyh2-1) and dominant counter selectable (Step 4: CYH2) markers in this strain reduces the background of contaminating diploid yeast following the meiotic assay to less than 1 in 10,000,000 cells. This lower background increases the probability of identify rare complementing cDNA clones.

The starting haploid strains are BY4741 (α, his3Δ, leu2Δ, met15Δ, ura3Δ) and BY4742 (α, his3Δ, leu2Δ, lys2Δ, ura3Δ)

Step 1. Modifying the CAN1 alleles in BY4741 and BY4742.

This step exploits the fact that both parental strains are sensitive to the arginine analog, canavanine. Consequently both strains can only grow on minimal plates supplemented by canavanine if the CAN1 gene is mutated, in this case by deletion. To accomplish, this each haploid strain is transformed with a can1 disruption fragment isolated from plasmid (pC3). The recombinant insert of this plasmid consists of the 5' and 3' flanking regions of the CAN1 open reading frame and provides several hundred base pairs of homology to the DNA sequences immediately upstream and downstream of the CAN1 translation initiation and stop codons respectively. These fragment to insert into the CAN1 locus thus deleting the CAN1 open reading frame.

To delete CAN1 from BY4741 and BY4742 the restriction fragment isolated from pC2 which carries the targeting sequences is used to transform the two parental strains using the transformation protocol outlined in Step 1 of Example 1. Transformants are selected for their ability to grow in minimal media containing 60 μg/ml canavanine. Deletion of the CAN1 open reading frame will be confirmed by Southern Blot analysis. The resulting genotypes are TC1 (α, can1Δ) and TC2 (α, can1Δ).

Step 2. Insertion of the CAN1 Dominant Counter Selectable Marker into TC1 (a, can1Δ).

The dominant counter selectable CAN1 marker will be inserted near the centromere of Chromosome I precisely as described in Step 2 of Example 1. The resulting Can$^s$ yeast strains thus carry a single copy of CAN1 (YAR002Ca::CAN1,HIS3::YAR003W) which serves as the dominant counter selectable marker (i.e. confers sensitivity to canavanine) and a deletion of the native CAN1 locus which serves as the haploid selecting recessive marker conferring resistance to canavanine. The resulting genotype of the resulting yeast strain is TC3 (α, can1Δ, YAR002Ca::CAN1,HIS3::YAR003)

Step 3. Introduction of the cyh2-1 cycloheximide Resistance Haploid Selecting Recessive Marker into TC3 (α, can1ΔYAR002Ca::CAN1,HIS3::YAR003W) and into TC2 (α, can1Δ,).

The wild type CYH2 allele is replaced by the cyh2-1 mutant allele in each of the strains. To accomplish this, the cyh2-1 allele along with the 5' and 3' flanking sequences is removed from the plasmid pC4 following restriction digestion. Plasmid C4 is constructed by cloning the cyh2-1 allele with about 400 base pairs of DNA on either side of the gene into pBluescript (Stratagene, Inc. San Diego, Calif.).

This DNA fragment is used to transform the two haploid yeast strains using the transformation protocol outline in Step 1 of Example 1. Transformants are selected based on their resistance to cycloheximide which is conferred by the cyh2-1 mutant allele. Since the wild type CYH2 allele is dominant and confers sensitivity to cycloheximide, only those transformants that have both lost the dominant wild type allele and incorporated the mutant cyh2-1 allele will survive the selection. The relevant genotype of the resulting haploid strains are TC5 ($\alpha$, can1$\Delta$, YAR002Ca::CAN1, HIS3::YAR003W cyh2-1) and into TC6 ($\alpha$, can1$\Delta$, cyh2-1) Step 4. Introduction of the Dominant Counter Selectable CYH2 Marker near the Chromosome VII Centromere of TC6 ($\alpha$, can1$\Delta$, cyh2-1).

To reduce the frequency of recombination between the CYH2 dominant sensitive marker and the centromere in subsequent meiotic assays, the CYH2 gene is placed in a position proximal to the chromosome VII centromere. To accomplish this, a plasmid, pC5 bearing the wildtype CYH2 allele and the HIS3 gene, both inserted between intergenic sequence linking the YGR001c and YGR002c yeast open reading frames is constructed. The insert isolated from pC5 serves as the source of the DNA fragment used to insert CYH2 adjacent near the centromere of chromosome IV.

A linear DNA fragment bearing the YGR001 c::CYH2, HIS3::YRG002c construct is used to transform TC6 ($\alpha$, can1$\Delta$, cyh2-1) following the transformation protocol outlined in Step 1 of Example 1. Transformants are identified by histidine prototrophy on minimal media lacking histidine. The resulting transformed yeast simultaneously become sensitive to cycloheximide and thus carry a single copy of CYH2. The CYH2 gene serves as a counter selectable marker which is dominant to the cyh2-1 haploid selecting recessive marker. The relevant genotype of the resulting haploid strain is TC7 ($\alpha$, can1$\Delta$, cyh2-1, YGR001c::CYH2, HIS3::YRG002c).

Step 5. Creating the CD1 Diploid Strain.

To generate the final CD1 diploid strain, the two haploid strains TC5 ($\alpha$, can1$\Delta$, YAR002Ca::CAN1, HIS3::YAR002W, cyh2-1) and TC7 ($\alpha$, can1$\Delta$, cyh2-1, YGR001c::CYH2,HIS3::YRG002c) are mated using standard protocols, creating the CD1 diploid with the genotype: ($\alpha$/$\alpha$, can1$\Delta$/can1$\Delta$, cyh2-1/cyh2-1, YAR002Ca::CAN1, HIS3::YAR003W, YGR001c::CYH2,HIS3::YRG002c/ YGR001c, YRG002c, his3$\Delta$1/his3$\Delta$1, leu2$\Delta$0leu2$\Delta$0, met15$\Delta$0/MET15, ura3$\Delta$0/ura3$\Delta$0, lys2$\Delta$0

Example 3

Isolation of CD1 Derivatives Carrying Multiple Mutations Which Together Display a Lethal Phenotype and Complementing the Lethality with a Heterologous Gene There are cases in yeast in which a single mutation results in death due to mutations in multiple genes. Often these mutations are in genes involved in a particular biochemical process or metabolic pathway none of which by itself defines a lethal phenotype. In these instances, one has essentially created new essential genes. Some of these essential genes are thus candidates for complementation by heterologous genes.

In this example, a derivative of the CD1 yeast strain is created which carries heterozygous deficiencies for both CIN8 and KIP1. The CIN8 and KIP1 gene products are both kinesin-related proteins involved in spindle body formation and maintenance. Haploid yeast of the genotype cin8$\Delta$, kip1$\Delta$ contain defective spindle bodies and are therefore nonviable because chromosomes segregate incorrectly during mitosis.

Step 1. Creating a CD1 Derivative Carry of Heterozygous CIN8/cin8 Deficiency.

One copy of CIN8 in the CD1 diploid is deleted by insertion of the KAN gene, which confers resistance to G418, into the CIN8 locus. This is accomplished by introducing a DNA fragment into CD1 by transformation (following the protocol outlined in Example 1 Step 1) and selecting for G418 resistance. The DNA fragment is generated by amplification of the KAN gene along with a yeast promoter from the plasmid pUG6. Two oligonucleotide primers are used for the amplification. One consists of 40 bp of homology to the 5' terminus of CIN8 coding sequence followed by 20 bp of homology to the 5' end of the promoter/KAN cassette of pUG6. The second primer consists of 40 bp which are complementary to the 3' terminus of the CIN8 coding sequence followed by 20 bp which are complementary to the 3' end of the promoter/KAN cassette of pUG6. The resulting amplification product consists of the promoter/KAN cassette flanked on either side by targeting sequences which direct integration of the DNA fragment to the CIN8 locus with the concomitant deletion of CIN8.

PCR amplification is used to confirm that the newly derived yeast strain is heterozygous for the cin8:KAN deletion. This is exploits the fact that native CIN8 and mutant cin8::KAN each produce a diagnostic product when genomic DNA is amplified using oligonucleotide primers which recognize sequences either upstream or downstream of the targeting sequences used for the disruption. One primer is homologous to 20 base pairs of sequence beginning 60 bp upstream of the CIN8 open reading frame and the other is complementary to 20 bp of sequence beginning 60 bp downstream of the CIN8. Because these CIN8 sequences were not included in the cin8::KAN disruption fragment, generation of the amplification product diagnostic for the cin8::KAN demonstrates the accuracy of the integration and corresponding cin8 disruption. No amplification product is evidence that the disruption fragment integrated into another site. Consequently in the desired heterozygote, two amplification products are produced, one for native CIN8 and the other for the cin8::KAN disruption. Strains homozygous for either the disruption or native CIN8 produce only the products diagnostic for the cin8::KAN or CIN8 respectively. The relevant genotype of the heterozygous diploid is CIN8/ cin8::KAN.

Step 2. Introducing the kip1 Deficiency Into CD1 (CIN8/ cin8::KAN).

Beginning with CD1 (leu2/leu2, CIN8/cin8::KAN) one copy of KIP1 will be disrupted using a kip1::LEU2 disruption DNA fragment generated from pRS405 which carries the LEU2 gene and a yeast promoter. The disruption fragment will again be generated by PCR amplification. In this case the 5' oligonucleotide primer will carry 40 bp of homology to the 5' terminus of the KIP1 ORF followed by 20 bp of homology to the 5' end of the promoter-Leu2 cassette. The 3' primer will carry 40 bp of complementary to the 3' terminus of the KIP1 ORF followed by 20 bp complementary to the 3 end of the promoter-LEU2 cassette. The 3' terminal 20 bp on either primer specific for the promoter-LEU2 cassette serves as the annealing sequence required for amplification from pRS405, and the 5' terminal 40 bp of KIP1 sequence serves as the element which targets integration of the DNA fragment into the KIP1 locus. The disruption fragment will be introduced by transformation as previously described (Example 1, Step 1) and LEU$^{2+}$ transformants are selected in minimal media lacking leucine.

Selected transformants are analyzed by PCR using a procedure analogous to that described for the cin8::KAN disruption (Example 3, step 1). In this case the oligonucleotide primers used will be derived from sequences 60 bp upstream or downstream of the KIP1 ORF and diploid yeast carrying the desired genotype produce amplification products diagnostic for both kip1::LEU2 and KIP1.

Step 3. Creating a Transformed Diploid Yeast Population.

The diploid yeast strain carrying the heterozygous deficiencies in CIN8 and KIP1 as well as the haploid selecting recessive markers (can1Δ/can1Δ; cyh2-1/cyh2-1) and the dominant counter selectable markers (YAR002Ca::CAN1HIS3::YAR003W, YGR001c::CYH2, HIS3::YRG002c) are transformed with a human cDNA library constructed in the yeast plasmid pBM272 in which cDNA fragments are cloned behind a GAL1 promoter. Transformation will follow the published protocol, selecting for Ura$^+$ cells (the selectable marker on pBM272). This procedure results in the generation of a heterogeneous population of yeast carrying library plasmids with a variety of cDNA inserts. The selection scheme described below in step 4 is designed to isolate from this heterogeneous yeast population, those transformed cells which harbor a plasmid carrying a human cDNA able to complement the cin8,kip1 deficiencies.

Step 4. Creating a Complemented Haploid Yeast Population.

The following mejotic complementation assay is used to isolate those yeast cells that harbor plasmids able to complement the cin8, kip1 deficiencies. This selection selects for meiotic products which carry each of the following genes: (i) the KAN$^r$ dominant selectable marker inserted into and inactivating CIN8, (ii) the LEU2 dominant selectable marker inserted into and inactivating KIP1, (iii) a library plasmid with a recombinant DNA insert capable of complementing the cin8 kip1 deficiency, (iv) the haploid selecting recessive, CAN$^r$, marker; and, (iv) the haploid selecting recessive cyh2-1 marker. To accomplish these goals the transformed diploid yeast population created as described in Example 3 is transferred to a medium that induces meiosis of S. cerevisiae precisely as described in Step 4 of Example 1. The sporulated cultures (10$^8$ cells per plate) are plated on medium containing canavinine, cycloheximide, and G418, lacking leucine, and containing galactose as a carbon source (and inducer of expression of the cDNA).

To survive on this medium cells must carry the KAN and LUE2 dominant selectable markers. They must also carry a human gene able to complement the cin8 kip1 deficiencies. Lastly, they must not carry either the CAN1 or CYH2 dominant counter selectable markers which confer sensitivity to canavanine and cycloheximide respectively. Diploids that failed to sporulate will perish on this medium because the carry the CAN1 CYH2 loci. One fourth of the spores will carry nether locus and thus be resistant to both selective agents. Such Can$^r$, Cyh$^r$ spores can only survive on the medium if they also carry the cin8::KAN and kip1::LEU2 loci that confer resistance to the G418 and leucine protrophy respectively. Because these spores must carry both the cin8 and kip1 disruptions, they will also perish unless they carry a human cDNA that complements these defects.

Although unlikely, some rare combinations of events can yield cells that survive on the final medium without a complementing plasmid. Mitotic recombination between the centromere and CAN1 on chromosome IV and between the centromere and the CYH2 locus on Chromosome VII can yield homozygous Can$^r$, Cyh$^r$ resistant diploids that can survive on the final medium. Additionally, meiotic segregation errors can yield Can$^4$, Cyh$^r$ hapolids that inherit both the cin8::KAN, kip1::LEU2 and either the CIN8 or KIP1 bearing chromosomes. Because of the multiplicity of independent events which must occur the unwanted background in this meiotic assay is virtually undetectable. Background events can be distinguished from complemented survivors because those that carry a complementing plasmid can not live without it. Dependence upon the complementing gene will be tested by plating on 5-FOA which selects against the URA3 marker carried on the transforming plasmid. Consequently complemented strains dependent on a plasmid borne gene can not grow in the presence of 5-FOA. Inhibition of growth on glucose which represses expression of the cDNA from the GAL4 promoter carried on the transforming plasmid will also be tested.

Step 5. Creating an Array of CD1 Strains Carrying Lethal Deficiencies which have Been Complemented by Human Genes.

An array of complemented yeast populations is created by repeating the steps detailed in steps 1–4 starting with a different yeast cell carrying multiple heterozygous deficiencies in different yeast genes that lead to a lethal phenotype. The result of this step will be the generation of a spatially ordered array of complemented yeast strains each dependent on expression of a different human cDNA for survival.

Example 4

Using the Target Array to Examine a Series of Chemical Compounds in Order to Determine the Activity, if any, and Target of that Activity, of Each of the Examined Compounds.

The strains are obtained using the method described above in Example 1. Each yeast strain comprising the array contains a human gene upon which the yeast strains are dependent for growth or other vital function because the yeast gene providing that function is inactive in the Target Array.

Step 1. Using the Array on a Solid Substratum.

Methods for testing drug sensitivities of microorganisms on nutrient agar containing test compounds are well established (Adams supra). The compound to be tested is added with mixing to molten nutrient agar. The compound is added at a concentration of 1 mM to 1 pM, preferably 10 uM to 1 nM. Each compound to be tested is added to a separate aliquot of molten agar. The molten nutrient agar is poured into plates or trays of the proper size for the number or strains to be tested. For example, for testing with an array of 10 to 100 strains, plastic plates of 25 cm diameter are appropriate. For testing with an array of 100 to 1,000 strains, plastic trays are appropriate. The molten agar is allowed to cool and harden.

The strains of the array to be used are spotted onto the surface of the substratum by replica plating from a master plate on which the strains have been grown. Alternatively, the strains of the array con be mechanically spotted on the array using arrays of pins or other automated systems to transfer aliquots of fluid medium containing the organisms to discrete spots on the substratum.

The plates or trays are placed under appropriate growth conditions, usually 30° C. and the growth of the yeast (rate of colony formation at the spotted area) is monitored by visual inspection or by automated densitometric analysis. Growth of individual strains are compared between plates containing a test compound and control plates with no test compound. The affect of a compound can be positive or negative. If the effect is positive colonies (cells) in the spot on the plate containing a compound grow faster than those on the corresponding spot on the control plate. If the affect is negative, growth is inhibited and colonies comprising a spot on a compound containing plate grow slower than those on the corresponding spot on the control plate. Compounds that affect the growth of one or a small number of strains are considered candidates for having specific action on the gene product of the foreign gene in each of the affected strain. Compounds which do not affect growth of any strain either have no activity on any of the gene products or are not able to penetrate the cell wall or membrane or are inactivated by a yeast function. Compounds affecting growth on all or nearly all of the strains of the array are considered active against one or more yeast gene products and hence, are not specific for a foreign gene product.

In this general method of testing compounds for their activities on a functional gene array, the yeast strains comprising the array are arrayed on a solid substrate such as a nutrient agar plate. The compounds to be tested are impregnated into a sheet of absorptive material and the sheet is layered onto the plate carrying the strains. The growth in number of cells or other parameter reflecting growth is followed. Compounds that affect the growth of one or a few of the strains of the array are candidates for having specific activity for the product of the foreign gene.

Step 2. Use of Arrays for Testing Compounds in Liquid Media.

Strains of the array are inoculated into wells or chambers of plates such as 96, 384, or 1536 well plates containing liquid growth medium or maintenance medium containing the compound to be tested. The basic and preferred media is YPD. Strains of the array are also inoculated into the wells of one or more control plates containing only the growth or maintenance medium.

The plates are placed under appropriate conditions for growth or maintenance, and the growth or other physiological parameter of the yeast strains is monitored. The growth or other physiological parameter of the strains treated with a compound are compared with the identical strains that are not treated. If the growth of one or a few strains differs between treated and untreated aliquots, the compound causing the effect is a candidate for having an activity that is specific for the gene product encoded by the foreign gene the affected strain or strains. As depicted in FIG. 3, screening of the Target Array with multiple compounds reveals specific inhibitor-target pairs. In this case Compound #1 specifically inhibited growth of the yeast strain dependent on expression of heterologous gene $D^H$ for survival indicating the this compound specifically inhibited the $D^H$ gene product. Similarly Compounds #2 and #3 inhibited the products of heterologous genes $B^H$ and $A^H$ respectively.

What is claimed is:

1. A stable haploid population of yeast cells having at least two selecting markers and a recombinant plasmid where:
   (a) the first marker is a dominant selectable marker wherein said marker is recombinantly inserted into an essential yeast gene rendering that essential gene inactive;
   (b) the second marker is a defined haploid-selecting recessive marker; and
   (c) the recombinant plasmid comprises a functional gene obtained from a genomic or cDNA library where the gene is a heterologous non-*Saccharomyces cerevisiae* gene that complements the essential gene inactivated by the dominant selectable marker.

2. A haploid population of claim 1 wherein the yeast is *Saccharomyces cerevisiae*.

3. A haploid population of claim 1 where the dominant selectable markers are selected from the group consisting of: KAN, LEU2, LYS2, URA3, TRP1, HIS3 and ADE2.

4. A haploid population of claim 1 wherein the defined haploid-selecting recessive marker is a selectable marker having a corresponding dominant counter selectable (sensitive) allele in the parental diploid yeast.

5. A haploid population of claim 1 where the haploid selecting recessive markers were generated by insertion or deletion which result in recessive selectable phenotypes.

6. A haploid population of claim 4 wherein the dominant counter selectable (sensitive) allele is a wild type allele selected from the group consisting of CAN1, CYH2, LYS2, MET15 and URA3.

7. A haploid population of claim 1 wherein the defined haploid-selecting recessive marker is a selectable marker from a group consisting of can1, cyh2-1, lys2, met15 and ura3.

8. A haploid population of claim 1 wherein the diploid population is less than one in 1,000,000.

9. A haploid population of claim 1 where the haploid population has a multiplicity of different dominant selectable markers inserted into more than one gene.

10. A haploid population of claim 4 wherein the yeast further comprise a second and different defined haploid-selecting recessive marker having a corresponding dominant counter selectable (sensitive) allele in the parental diploid yeast.

11. An array of individual members where the members are stable haploid populations of yeast cells having at least two selectable markers and a recombinant plasmid where:
   (a) the first marker is a dominant selectable marker wherein said marker is recombinantly inserted into an essential yeast gene rendering that essential gene inactive;
   (b) the second marker is a defined haploid-selecting recessive marker; and
   (c) the recombinant plasmid comprises a functional gene that complements the essential gene inactivated by the dominant selectable marker; and,
   wherein at least two members of the array have the dominant selectable marker inserted into and inactivating a different essential yeast gene and the functional gene of the recombinant plasmid is different.

12. An array of claim 11 wherein the yeast is *Saccharomyces cerevisiae*.

13. An array of claim 11 where the dominant selectable markers are selected from the group consisting of: KAN, LEU2, LYS2, URA3, TRP1, HIS3 and ADE2.

14. An array of claim 11 wherein the defined haploid-selecting recessive marker is a selectable marker having a corresponding dominant counter selectable (sensitive) allele in the parental diploid yeast.

15. An array of claim 11 wherein the dominant counter selectable (sensitive) allele is a wild type allele selected from the group consisting of CAN1, CYH2, LYS2, MET15 and URA3.

16. An array of claim 11 where the haploid selecting recessive markers were generated by an insertion, deletion or point mutation which resulted in recessive selectable phenotypes.

17. An array of claim 11 wherein the defined haploid selecting recessive marker is a selectable marker selected from a group consisting of can1, cyh2-1, lys2, met15 and ura3.

18. An array of claim 11 where the functional genes on the plasmids are heterologous genes from a non-*Saccharomyces cerevisiae* organism.

19. An array of claim 11 where the members have a multiplicity of different dominant selectable markers inserted into more than one gene and inactivating those genes.

20. An array of claim 11 wherein members carry a second dominant selectable marker different than said first marker where the second dominant selectable marker is operably linked to a haploid specific promoter.

21. A population of diploid yeast cells having at least two recombinant insertions and transformed by at least one recombinant plasmid where:
   (a) the first insertion is a dominant selectable marker said marker inserted into an essential yeast gene rendering that essential gene inactive; and,
   (b) the second recombinant insertion is a single copy of a dominant counter selectable (sensitive) marker and is allelic to a corresponding haploid-selecting recessive marker in the parental diploid yeast.

22. The yeast cell of claim 21, where the cell has two haploid selecting recessive markers.

23. A yeast cell of claim 21 where the dominant counter selectable marker is selected from the group consisting of: CAN1, CYH2, URA3, LYS2 and MET15 and the corresponding recessive alleles are selected from the corresponding allele consisting of can1, cyh2-1, ura3, lys2, and met 15.

24. A yeast cell of claim 21 wherein the yeast is *Saccharomyces cerevisiae*.

25. A yeast cell of claim 21 where the dominant selectable markers are selected from the group consisting of: KAN, LEU2, LYS2, URA3, TRP1, HIS3 and ADE2.

26. A yeast cells of claim 21 where the haploid selecting recessive markers were generated by insertion or deletion.

27. A diploid yeast cell having the following recombinant insertions:
   (a) a first insertion that is a dominant selectable marker said marker inserted into an essential yeast gene rendering that essential gene inactive;
   (b) a second recombinant insertion positioned within 5 centimorgans of a centromere where the insertion is a single copy of a first dominant counter selectable marker that is allelic to a corresponding recessive selectable marker and;
   a third recombinant mutation that is introduced to the native copies of the gene corresponding to the first dominant counter selectable marker and renders those loci recessive selectable markers.

28. A yeast cell of claim 27 wherein the third recombinant mutation is introduced into two native copies of the gene corresponding to the first dominant counter selectable marker.

29. A yeast cell of claim 27 having a fourth recombinant insertion within approximately 5 centimorgans of a centromere of a different chromosome than that of the second recombinant insertion and that is a single copy of a second and different dominant counter selectable marker and a fifth recombinant mutation that is introduced into the native copies of the gene corresponding to the second dominant counter selectable marker, and renders those loci recessive selectable markers.

30. A yeast cell of claim 27 wherein the yeast is *Saccharomyces cerevisiae*.

31. A method of determining the gene encoding the target of a biologically active compound comprising the steps of:
   (A) creating an array of stable haploid populations of yeast cells having at least two selecting markers and a recombinant plasmid wherein:
      (a) the first marker is a dominant selectable marker wherein said marker is recombinantly inserted into an essential yeast gene rendering that essential gene inactive where the members of the array have different essential genes inactivated;
      (b) the second marker is a defined haploid-selecting recessive marker; and
      (c) the recombinant plasmid comprises a functional heterologous gene that complements the essential gene inactivated by the dominant selectable marker;
      (d) the haploid population is derived from a population of diploid yeast cells having at least two recombinant insertions and transformed by at least one recombinant plasmid where:
         (i) the first insertion is a dominant selectable marker said marker inserted into an essential yeast gene rendering that essential gene inactive; and,
         (ii) the second recombinant insertion is a single copy of a dominant counter selectable (sensitive) marker and is allelic to a corresponding haploid-selecting recessive marker in the parental diploid yeast; and,
      (e) populations within the array are dependent upon different heterologous genes for survival;
   (B) contacting the array with the biologically active compound in an amount that produces a compound-specific reaction with a population of the array but not with all populations, and,
   (C) determining the yeast population within the array that is reactive to the compound.

32. A method of claim 31 wherein the diploid yeast cell carries a second dominant selectable marker that is different than the marker of the first insertion where said second dominant selectable marker is operably linked to a haploid specific promoter.

33. A method of claim 31 wherein the dominant selectable marker is recombinantly inserted into different essential yeast genes.

34. A method of claim 31 where the dominant selectable markers are selected from the group consisting of: KAN, LEU2, LYS2, URA3, TRP1, HIS3 and ADE2.

35. A method of claim 31 wherein the dominant counter selectable (sensitive) allele is selected from the group consisting of CAN1, CYH2, LYS2, MET15 and URA3.

36. A method of claim 31 wherein the yeast is *Saccharomyces cerevisiae*.

37. An array of individual members where the members are stable haploid populations of yeast cells having at least two selectable markers and a recombinant plasmid where:
   (a) the first marker is a dominant selectable marker wherein said marker is recombinantly inserted into an essential yeast gene rendering that essential gene inactive;
   (b) the second marker is a defined haploid-selecting recessive marker; and
   (c) the recombinant plasmid comprises a functional gene that complements the essential gene inactivated by the dominant selectable marker; and,
   wherein at least two members of the array have the dominant selectable marker inserted into and inactivating a different essential yeast gene or at least two members of the array have the dominant selectable marker in the same essential gene and the functional gene of the recombinant plasmid is different.

38. A method of claim 31 wherein functional heterologous gene on the recombinant plasmid is a naturally occurring gene.

39. A haploid population of claim 31 wherein the functional gene on the recombinant plasmid is obtained from a genomic or cDNA library.

40. A method of identifying a compound with activity for a specific protein product of a functional heterologous gene that complements an essential gene without activity upon other protein products comprising the steps of:
  (i) creating an array of stable haploid populations of yeast cells having at least two selecting markers and a recombinant plasmid where:
    (a) the first marker is a dominant selectable marker wherein said marker is recombinantly inserted into an essential yeast gene rendering that essential gene inactive where the members of the array have different essential genes inactivated;
    (b) the second marker is a defined haploid-selecting recessive marker; and,
    (c) the recombinant plasmid comprises a functional heterologous gene that complements the essential gene inactivated by the dominant selectable marker;
  where populations within the array are dependent upon different heterologous genes for survival each population defining a different member of the array;
  (ii) contacting the array with biologically active compounds in an amount that can produce a compound-specific reaction with a population of the array but not with all populations and,
  (iii) identifying a compound that reacts specifically with one member of the array but not with other members of the array.

41. A method of claim 40 wherein the haploid populations are derived from a population of diploid yeast cells having at least two recombinant insertions and transformed by at least one recombinant plasmid where:
  (a) the first insertion is a dominant selectable marker said marker inserted into an essential yeast gene rendering that essential gene inactive; and,
  (b) the second recombinant insertion is a single copy of a dominant counter selectable (sensitive) marker and is allelic to a corresponding haploid-selecting recessive marker in the parental diploid yeast.

* * * * *